United States Patent
Arcand et al.

(10) Patent No.: US 11,191,888 B1
(45) Date of Patent: Dec. 7, 2021

(54) SYRINGE-BASED MICROBUBBLE GENERATOR

(71) Applicant: Agitated Solutions Inc., Oakdale, MN (US)

(72) Inventors: Benjamin Arcand, Minneapolis, MN (US); Carl Lance Boling, San Jose, CA (US)

(73) Assignee: Agitated Solutions Inc., Oakdale, MN (US)

( * ) Notice: Subject to any disclaimer, the term of this patent is extended or adjusted under 35 U.S.C. 154(b) by 0 days.

(21) Appl. No.: 17/158,396

(22) Filed: Jan. 26, 2021

(51) Int. Cl.
  *A61M 5/00* (2006.01)
  *A61K 49/22* (2006.01)
  *A61M 5/145* (2006.01)
  *A61M 5/14* (2006.01)

(52) U.S. Cl.
  CPC ........... *A61M 5/007* (2013.01); *A61K 49/223* (2013.01); *A61M 5/00* (2013.01); *A61M 5/1452* (2013.01); *A61M 5/1408* (2013.01)

(58) Field of Classification Search
  CPC ....... A61K 49/223; A61M 5/00; A61M 5/007; A61M 5/1452; A61M 5/1408; A61M 2005/3106
  See application file for complete search history.

(56) References Cited

U.S. PATENT DOCUMENTS

| 4,406,656 A | 11/1983 | Hattler et al. |
| 4,705,508 A | 11/1987 | Karnavas et al. |
| 4,844,882 A | 7/1989 | Widder et al. |

(Continued)

FOREIGN PATENT DOCUMENTS

| CN | 101032514 A | 9/2007 |
| CN | 106731840 A | 5/2017 |

(Continued)

OTHER PUBLICATIONS

Alung Technologies, "Use of the Hattler Respiratory Assist Catheter in Severe Respiratory Failure," retrieved from https://clinicaltrials.gov/ct2/show/NCT00288964, last visited Jan. 21, 2021, 3 pages.

(Continued)

*Primary Examiner* — Emily L Schmidt
*Assistant Examiner* — Leah J Swanson
(74) *Attorney, Agent, or Firm* — Matthew J. Smyth

(57) ABSTRACT

A device for generating microbubbles may include a syringe having a barrel, a plunger and a syringe tip; a converging nozzle; and an aerator. The converging nozzle may have a coupling end, a converging tip opposite the coupling end, an exterior mating surface adjacent the converging tip, and an interior channel that fluidly couples the syringe tip and converging tip. The interior channel may have a diameter that progressively decreases from the coupling end to the converging tip. The converging nozzle may be coupled to the syringe tip. The aerator may have a retention end, a discharge end, an interior air chamber, an interior circumferential lip, and a discharge channel at the discharge end. The retention end may be coupled to the converging nozzle. The interior circumferential lip may abut the exterior mating surface. One or more air channels may fluidly couple the discharge channel and the interior air chamber.

21 Claims, 7 Drawing Sheets

(56) References Cited

U.S. PATENT DOCUMENTS

| | | | |
|---|---|---|---|
| 4,986,809 A | 1/1991 | Hattler | |
| 5,098,376 A | 3/1992 | Berry et al. | |
| 5,265,593 A | 11/1993 | Odland | |
| 5,271,743 A | 12/1993 | Hattler | |
| 5,376,069 A | 12/1994 | Hattler | |
| 5,409,688 A | 4/1995 | Quay | |
| 5,433,711 A * | 7/1995 | Balaban | A61M 5/3202 |
| | | | 604/192 |
| 5,501,663 A | 3/1996 | Hattler et al. | |
| 5,605,673 A | 2/1997 | Schutt et al. | |
| 5,686,060 A | 11/1997 | Schneider et al. | |
| 5,749,829 A * | 5/1998 | Yokoi | A61B 1/00068 |
| | | | 600/153 |
| 5,823,180 A | 10/1998 | Zapol | |
| 5,865,789 A | 2/1999 | Hattler | |
| 5,938,634 A | 8/1999 | Packard | |
| 6,261,537 B1 | 7/2001 | Klaveness et al. | |
| 6,350,249 B1 | 2/2002 | Zicherman | |
| 6,450,963 B1 | 9/2002 | Ackerman | |
| 6,537,246 B1 | 3/2003 | Unger et al. | |
| 6,572,840 B1 | 6/2003 | Toler | |
| 8,021,359 B2 | 11/2011 | Auth et al. | |
| 8,063,020 B2 | 11/2011 | Simpkins | |
| 8,167,280 B2 | 5/2012 | Chomas et al. | |
| 8,282,967 B2 | 10/2012 | Schoenfisch et al. | |
| 8,260,411 B1 | 11/2012 | Odland et al. | |
| 8,367,613 B2 | 2/2013 | Simpkins | |
| 8,419,674 B2 | 4/2013 | Cattaneo et al. | |
| 8,470,298 B2 | 6/2013 | Uber, III et al. | |
| 8,574,309 B2 | 11/2013 | Galea et al. | |
| 8,579,880 B2 | 11/2013 | Grady et al. | |
| 8,622,911 B2 | 1/2014 | Hossack et al. | |
| 8,647,569 B1 | 2/2014 | Federspiel et al. | |
| 8,939,436 B2 | 1/2015 | Takase et al. | |
| 9,022,974 B2 | 5/2015 | Rinehart et al. | |
| 9,061,255 B2 | 6/2015 | Song et al. | |
| 9,700,680 B2 * | 7/2017 | Sharma | A61M 5/31596 |
| 9,845,237 B2 | 12/2017 | Tseng et al. | |
| 10,124,126 B2 | 11/2018 | Borden et al. | |
| 10,335,530 B2 | 7/2019 | Madhani et al. | |
| 10,577,554 B2 | 3/2020 | Kheir et al. | |
| 10,646,507 B2 | 3/2020 | Poetzschke et al. | |
| 2001/0002993 A1 | 6/2001 | Ostensen et al. | |
| 2004/0141921 A1 | 7/2004 | Ostensen et al. | |
| 2005/0260189 A1 | 11/2005 | Klibanov et al. | |
| 2006/0273695 A1 | 12/2006 | Savage | |
| 2007/0059247 A1 | 3/2007 | Lindner et al. | |
| 2008/0262413 A1 | 10/2008 | Ladizinsky | |
| 2010/0228122 A1 | 9/2010 | Keenan et al. | |
| 2010/0224191 A1 | 11/2010 | Dixon et al. | |
| 2011/0020236 A1 | 1/2011 | Bohmer et al. | |
| 2011/0270156 A1 | 11/2011 | Hassan et al. | |
| 2012/0226258 A1 | 9/2012 | Otto et al. | |
| 2013/0207285 A1 | 8/2013 | Cooke | |
| 2014/0010848 A1 | 1/2014 | Kheir et al. | |
| 2014/0155745 A1 * | 6/2014 | Duncan | A61M 39/10 |
| | | | 600/435 |
| 2015/0133779 A1 * | 5/2015 | Yurek | A61B 8/12 |
| | | | 600/435 |
| 2015/0164787 A1 | 6/2015 | Kheir et al. | |
| 2016/0067276 A1 | 3/2016 | Polizzotti et al. | |
| 2016/0287809 A1 | 10/2016 | Sharma | |
| 2018/0104146 A1 * | 4/2018 | Tachibana | A61J 1/14 |
| 2019/0314567 A1 | 10/2019 | Straube et al. | |

FOREIGN PATENT DOCUMENTS

| | | |
|---|---|---|
| CN | 110279432 A | 9/2019 |
| CN | 110243454 A | 6/2020 |
| DE | 19622184 A1 | 12/1997 |
| DE | 10341221 A1 | 3/2005 |
| EP | 3041495 A1 | 7/2016 |
| IN | 311914 B | 12/2012 |
| JP | H0621538 Y2 | 6/1994 |
| JP | 5470630 B2 | 4/2014 |
| JP | 6653185 B1 | 2/2016 |
| WO | 2002076530 A1 | 3/2002 |
| WO | 2005028002 A1 | 3/2005 |
| WO | 2006066553 A8 | 6/2006 |
| WO | 2008019102 A2 | 2/2008 |
| WO | 2008147050 A1 | 12/2008 |
| WO | 2012108855 A1 | 6/2012 |
| WO | 2019173387 A1 | 9/2019 |
| WO | 2020123791 A1 | 6/2020 |

OTHER PUBLICATIONS

Alung, "Vent-Avoid Trial," retrieved from https://www.alung.com/healthcare-professionals-us/, last visited Feb. 1, 2021, 2 pages.

Gekle et al., "Saline Flush Test: Can Bedside Sonography Replace Conventional Radiography for Confirmation of Above-the-Diaphragm Central Venous Catheter Placement," J Ultrasound Med. 2015, 34: 1295-1299, 5 pages.

Horowitz et al., "The FLUSH Study—Flush the Line and Ultrasound the Heart: Ultrasonographic Confirmation of Central Femoral Venous Line Placement," Annals of Emergency Medicine 2014, 63(6): 678-683, 6 pages.

Passos et al.,"Agitated Saline Bubble—Enhanced Ultrasound for Assessing Appropriate Position of ?Hemodialysis Central Venous Catheter in Cilically III Patients," Kidney International Reports 2017, 2: 952-968, 5 pages.

Wilson et al., "Simplified point-of-care ultrasound protocol to confirm central venous catheter placement: A prospective study," World J Emerg Med 2017, 8(1): 25-28, 4 pages.

Bhadran, V. & Goharzadeh, A., "Monodispersed microbubble production using modified micro-Venturi bubble generator," AIP Advances 10, 095306 (2020).

Fujiwara, A et al., "Bubble Breakup Phenomena in a Venturi Tube," ASME, 8(2007), 8 pages.

Huang, J. et al., "A review on bubble generation and transportation in Venturi-type bubble generators," Tsinghua University Press 2019, 12, 12 pages.

Lee, C. H. et al.., "Experimental investigation of microbubble generation in the venturi nozzle," International Journal of Heat and Mass Transfer 136, 1127-1138 (2019), 12 pages.

Liew, K.C.S. et al., "Porous Venturi-Orifice Microbubble Generator for Oxygen Sissolution in Water," Processes, 15 (2020), 15 pages.

Acandis, Catheters, retrieved from https://www.acandis.com/catheters-34-en&print_view=1, last visited Jan. 21, 2021, 2 pages.

Admedes, Venous Stents, retrieved from https://www.admedes.com/en/ideas, last visited Jan. 21, 2021, 4 pages.

Associated Press, "What tiny air bubbles are teaching doctors about how COVID-19 damages the lungs," LA Times (AP), Aug. 19, 2020, retrieved from https://www.latimes.com/science/story/2020-08-19/tiny-bubbles-lead-scientists-to-new-coronavirus-clue-lung-damage, last visited Jan. 21, 2021, 9 pages.

Boston Scientific, Biliary Access, https://www.bostonscientific.com/content/dam/bostonscientific/endo/catalog/2018/Biliary-Access.pdf, last visited Jan. 27, 2021, 13 pages.

Cattaneo et al., "Intravascular Blood Oxygenation Using Hollow Fibers in a Disk-Shaped Configuration: Experimental Evaluation of the Relationship Between Porisity and Performance," ASSAIO Journal 2006, p. 180-185., 6 Pages.

Cook, EchoTip, retrieved from https://www.cookmedical.com/products/wh_opsd_webds/, last visited Jan. 21, 2021, 4 pages.

Elson et al.,"Development of an intravenous oxygenator using microbubbles," 2014 Cairo International Biomedical Engineering Conference, retrieved from https://ieeexplore.ieee.org/document/7020920, last visited Jan. 21, 2021, 2 pages.

Fresenius Medical Care, Novalung, https://fmcna.com/products/critical-care/novalung/, last visited Jan. 21, 2021, 9 pages.

Green, "Nitric Oxide, BCG, and COVID-19's Weakness," Medpage Today, May 10, 2020, retrieved from https://www.medpagetoday.com/infectiousdisease/covid19/86410?xid=nl_popmed_2020-05-14&eun=g386429d0r&utm_source=Sailthru&utm_medium=email

(56) References Cited

OTHER PUBLICATIONS

&utm_campaign=PopMedicineWinner_051420&utm_content=Final &utm_term=NL_Gen_Int_PopMedicine_Active), last visited Jan. 21, 2021, 9 pages.

Hattler et al., "A respiratory gas exchange catheter: In vitro and in vivo tests in large animals," J Thorac and Card Sur 2002, p. 520-530., 11 pages.

Helix2, Double Lumen Needles, retrieved from http://helix2.gr/double-lumen-needles/, last visited Jan. 21, 2021, 2 pages.

Hettiarachchi et al., "On-chip generation of microbubbles as a practical technology for manufacturing contrast agents for ultrasonic imaging," Lab Chip 2007, 7(4): 463-468, retrieved from https://www.ncbi.nlm.nih.gov/pmc/articles/PMC2253663/pdf/nihms-26478.pdf, last visited Jan. 21, 2021, 14 pages.

Huang et al., "Morphometry of the human pulmonary vasculature," The American Psychological Society 1996, 2123-2133, retrieved from https://pdfs.semanticscholar.org/ed0f/258bd8e53b840fb701461cd2b8cf8e83b0e0.pdf?_ga=2.129795084.1468030525.1611250726-820194694.1611250726, last visited Jan. 21, 2021, 11 pages.

IVF Future, Steiner Tan Needle, https://www.ivffuture.com/steiner-tan-needle/, last visited Jan. 21, 2021, 4 pages.

Khan et al., "Engineering oxygen nanobubbles for effective reversal of hypoxia," Artificial Cells, Nanomedicine, and Biotechnology, 2018, vol. 46, No. S3, S318-S327, retrieved from https://www.tandfonline.com/doi/pdf/10.1080/21691401.2018.1492420?needAccess=true, last visited Jan. 21, 2021, 11 pages.

Kheir, "Building a better bubble: engineering tweaks bring safe IV oxygen delivery closr to reality," Vector, Boston Children's Hospital's science and clinical innovation blog, retrieved from https://vector.childrenshospital.org/2018/02/building-better-oxygen-bubbles/, last visited Jan. 21, 2021, 7 pages.

Matsuki et al., "Oxygen supersaturated fluid using fine micro/nanobubbles," International Journal of Nanomedicine, 2014; 9:4495-4505, retrieved from https://www.ncbi.nlm.nih.gov/pmc/articles/PMC4181745/, last visited Jan. 27, 2021, 11 pages.

Nall, Rachel, "What is the Valsalva Maneuver?," Medical News Today, Aug. 2, 2018, retrieved from https://www.medicalnewstoday.com/articles/322661, last visited Jan. 28, 2021, 17 pages.

Rocket Medical, Rocket Double Lumen Oocyte Aspiration Needles, retrieved from https://sales.rocketmedical.com/rocket-double-lumen-oocyte-aspiration-needles, last visited Jan. 21, 2021, 2 pages.

Singhal et al., "Morphometry of the Human Pulmonary Arterial Tree," Circulation Research 1973, 33:190-197, retrieved from https://www.ahajournals.org/doi/pdf/10.1161/01.RES.33.2.190, 8 pages.

Toffaletti et al., "Effect of small air bubbles on changes in blood pO2 and blood gas parameters: calculated vs. measured effects," retrieved from https://acutecaretesting.org/en/articles/effect-of-small-air-bubbles-on-changes-in-blood-po2-and-blood-gas-parameters, last visited Jan. 21, 2021, 8 pages.

Vitrolife, Double Lumen, https://www.vitrolife.com/products/oocyte-retrieval-needles/double-lumen/, last visited Jan. 21, 2021, 5 pages.

\* cited by examiner

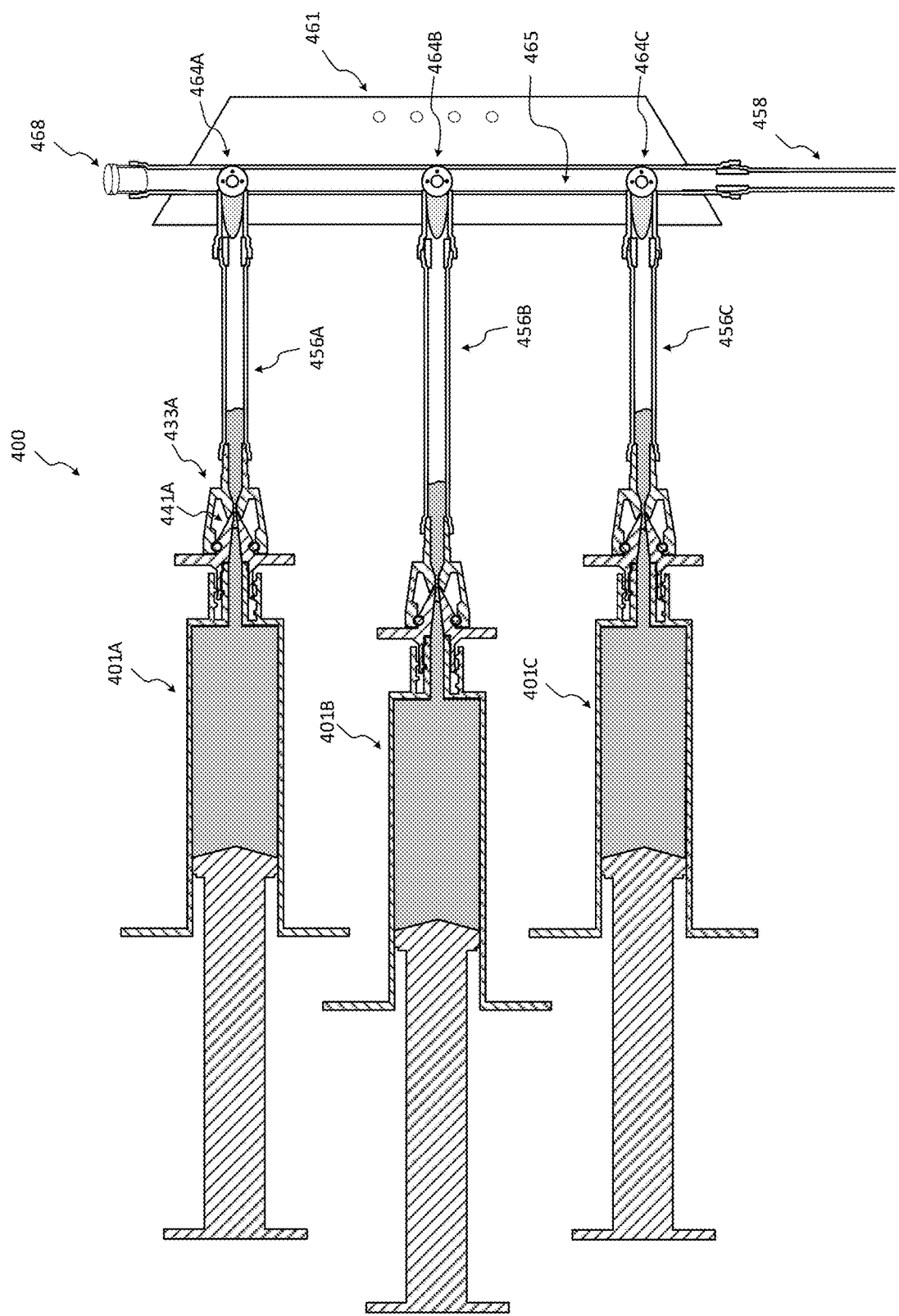

ND MICROBUBBLE
SYRINGE-BASED MICROBUBBLE GENERATOR

TECHNICAL FIELD

Various implementations relate generally to generating microbubbles for use in various diagnostic and therapeutic procedures.

BACKGROUND

Echocardiography refers to the use of ultrasound to study the heart. Echocardiography is a widely used diagnostic test in the field of cardiology and may be used in the diagnosis, management, and follow-up of patients with suspected or known heart diseases. The results from an echocardiography test may provide much helpful information, including the size and shape of the heart's components (e.g., internal chamber size quantification), pumping function, and the location and extent of any tissue damage. An echocardiogram may also give physicians other estimates of heart function, such as a calculation of the cardiac output, ejection fraction (the percentage of blood volume of the left ventricle that is pumped out with each contraction), diastolic function (how well the heart relaxes), etc.

Echocardiography may be performed in one of multiple ways. Least invasively, an ultrasound transducer may be placed on a patient's chest, and imaging may be done through the patient's chest wall, in a transthoracic echocardiogram (TTE). If a higher fidelity image is required, a more invasive transesophageal echocardiogram (TEE) may be performed, in which an ultrasound transducer disposed on a thin tube is placed down the patient's throat and into the esophagus. Because the esophagus is so close to the heart, this procedure can be employed to secure very clear images of heart structures and valves.

During either a TTE or TEE procedure, a contrast agent may be employed to enhance the imaging of the procedure. This contrast agent may be injected into the patient's vein, such that it quickly reaches the chambers of the heart and is detected by ultrasound to give greater definition to structures of the heart. In some procedures, the contrast agent employed is a saline solution comprising tiny air bubbles, and the procedure may be referred to as an agitated saline contrast study or "bubble study."

SUMMARY

In some implementations, a device for generating microbubbles includes a syringe having a barrel, a plunger and a syringe tip; a unitary component having a converging nozzle and aerator; and a housing surrounding the unitary component. The housing may form an air chamber between an interior surface of the housing and an exterior surface of the unitary component.

The converging nozzle may have a coupling end, a converging tip opposite the coupling end, and an interior channel that fluidly couples the coupling end and converging tip. The interior channel may have a diameter that progressively decreases from the coupling end to the converging tip. The converging nozzle may be coupled to the syringe tip at its coupling end. The aerator may have an inlet that is axially aligned with the interior channel and a discharge channel that is fluidly coupled to the inlet. The unitary component may further include one or more air channels that fluidly couple the air chamber and a region adjacent the converging tip and the inlet.

The device may further include one or more seals that isolate the air chamber from a region exterior to the housing from ingress or egress of gas or liquid via any path other than through the one or more air channels. In some implementations, the one or more seals are one or more O-rings. The syringe may be a medical-grade syringe having a capacity of 1 mL, 2 mL, 3 mL, 5 mL, 10 mL or 20 mL. At least one of a dimension, a geometry or a surface treatment of the one or more air channels, the converging tip or the inlet may be configured to facilitate creation of microbubbles having a surface tension or charge that minimizes coalescence of microbubbles after they are generated.

In some implementations, at least one of a dimension, a geometry or a surface treatment of the one or more air channels, the converging tip or the inlet may be configured to facilitate creation of microbubbles having an average diameter of about 40 µm or less or about 100 µm or less; or an average diameter of about 5 µm to about 10 µm; or an average diameter of about 2 µm or less.

In some implementations, a device for generating microbubbles (e.g., for use as a contrast agent) includes a syringe having a barrel, a plunger and a syringe tip; a converging nozzle; and an aerator. The converging nozzle may have a coupling end, a converging tip opposite the coupling end, an exterior mating surface adjacent the converging tip, and an interior channel that fluidly couples the syringe tip and converging tip. The interior channel may have a diameter that progressively decreases from the coupling end to the converging tip. The converging nozzle may be coupled to the syringe tip at its coupling end. The aerator may have a retention end, a discharge end, an interior air chamber, an interior circumferential lip, and a discharge channel at the discharge end. The retention end may be coupled to the converging nozzle. The interior circumferential lip may abut the exterior mating surface. The interior circumferential lip may be disposed adjacent the exterior mating surface. One or more air channels may fluidly couple the discharge channel and the interior air chamber.

In some implementations, each of the one or more air channels is parallel to the exterior mating surface. At least one of a dimension, a geometry or a surface treatment of the one or more air channels may be configured to facilitate creation of microbubbles having an average diameter of about 5 µm to about 10 µm, in some implementations. In other implementations, at least one of a dimension, a geometry or a surface treatment of the one or more air channels may configured to facilitate creation of microbubbles having an average diameter of about 2 µm or less; in still other implementations, at least one of a dimension, a geometry or a surface treatment of the one or more air channels may be configured to facilitate creation of microbubbles having a surface tension or charge that minimizes coalescence of microbubbles after they are generated.

The converging nozzle and aerator may each comprise O-ring retention channels, and the aerator and converging nozzle may be coupled by an O-ring seated in the O-ring retention channels. The converging nozzle and aerator may be coupled with an adhesive or by an ultrasonic weld. The syringe and converging nozzle may be coupled with an adhesive or by an ultrasonic weld. The syringe and converging nozzle may be co-molded together. The syringe tip and coupling end may include mating Luer fittings.

The device may further include a removable retention pin that, when seated, prevents fluid communication between the interior air chamber and the discharge channel or interior channel. The removable retention pin may provide a sterile seal that protects the discharge channel.

In some implementations, a method of generating microbubbles may include providing a microbubble generator having (a) a syringe with a barrel that is filled with a body-compatible fluid, a plunger and a syringe tip; (b) a converging nozzle; and (c) an aerator; coupling the discharge end to an intravenous line disposed in a patient undergoing a procedure; and generating microbubbles by forcing the body-compatible fluid out of the syringe and through the converging nozzle and aerator, into a discharge channel. The method may further include extracting a removable retention pin from the discharge channel.

The converging nozzle may have a coupling end, a converging tip opposite the coupling end, an exterior mating surface adjacent the converging tip, and an interior channel that fluidly couples the syringe tip and converging tip. The interior channel may have a diameter that progressively decreases from the coupling end to the converging tip. The converging nozzle may be coupled to the syringe tip at the coupling end. The aerator may include a retention end, a discharge end, an interior air chamber, an interior circumferential lip, and a discharge channel at the discharge end. The retention end may be coupled to the converging nozzle. The interior circumferential lip may abut the exterior mating surface. The interior circumferential lip may be disposed adjacent the exterior mating surface. One or more air channels may fluidly couple the discharge channel and the interior air chamber.

The progressively decreasing diameter may cause, via the Venturi effect, air to be extracted from the interior air chamber, via the one or more air channels, thereby creating microbubbles. The body-compatible fluid may be saline or dextrose. The removable retention pin, prior to its removal, may prevent fluid communication between the interior air chamber and the discharge channel or interior channel.

In some implementations, a method of generating microbubbles includes providing a microbubble generator having (a) a syringe having a barrel filled with a body-compatible fluid, a plunger and a syringe tip; (b) a converging nozzle and aerator; and (c) a housing surrounding the converging nozzle and aerator to form an air chamber between an interior surface of the housing and exterior surfaces of the converging nozzle and aerator. The converging nozzle may have a coupling end, a converging tip opposite the coupling end, and an interior channel that fluidly couples the coupling end and converging tip and has a diameter that progressively decreases from the coupling end to the converging tip. The converging nozzle may be coupled to the syringe tip at its coupling end. The aerator may have an inlet that is axially aligned with the interior channel and a discharge channel that is fluidly coupled to the inlet. The aerator may further include one or more air channels that fluidly couple the air chamber and a region adjacent the converging tip and the inlet. The method may further include coupling the discharge channel to an intravenous line disposed in a patient undergoing a procedure; and generating microbubbles by forcing the body-compatible fluid out of the syringe and through the converging nozzle and aerator, into the discharge channel.

In some implementations, the diameter that progressively decreases may cause, via the Venturi effect, air to be extracted from the air chamber, via the one or more air channels, thereby creating microbubbles. In some implementations, the body-compatible fluid may be saline or dextrose.

In some implementations, a system for generating microbubbles includes a plurality of microbubble generators and a manifold having at least as many inlet ports as microbubble generators in the plurality of microbubble generators. Each of the plurality of microbubble generators may be coupled to an inlet port in the manifold. The manifold may further include an outlet port configured for coupling to an intravenous line associated with a patient undergoing a procedure. The manifold may include a valve for each inlet port that is configured to permit fluid coupling to or isolation from a corresponding microbubble generator and the outlet port.

Each microbubble generator may have (a) a syringe with a barrel that is filled with a body-compatible fluid, a plunger and a syringe tip; (b) a converging nozzle; and (c) an aerator. The converging nozzle may have a coupling end, a converging tip opposite the coupling end, an exterior mating surface adjacent the converging tip, and an interior channel that fluidly couples the syringe tip and converging tip. The interior channel may have a diameter that progressively decreases from the coupling end to the converging tip. The converging nozzle may be coupled to the syringe tip at the coupling end. The aerator may include a retention end, a discharge end, an interior air chamber, an interior circumferential lip, and a discharge channel at the discharge end. The retention end may be coupled to the converging nozzle. The interior circumferential lip may abut the exterior mating surface. The interior circumferential lip may be disposed adjacent the exterior mating surface. One or more channels fluidly may couple the discharge channel and the interior air chamber.

In some implementations, at least one of the plurality of microbubble generators is configured to generate microbubbles having a first average diameter, and at least another one of the plurality of microbubble generators is configured to generate microbubbles having a second average diameter, wherein the first average diameter is larger than the second average diameter.

BRIEF DESCRIPTION OF THE DRAWINGS

FIG. 4 illustrates an exemplary microbubble generating system.

DETAILED DESCRIPTION

Agitated saline contrast studies (or "bubble studies") are a useful adjunct to many ultrasound examinations, particularly cardiac ultrasound (echocardiography). Injection of agitated saline into a vein combined with echocardiography is a validated method to detect shunts which may be within the heart such as a patent foramen ovale, (PFO) or an atrial septal defect (ASD)—two types of holes in the heart—or external to the heart (e.g., in the lungs) known as pulmonary arteriovenous malformations (pAVM). Agitated saline can also be used with echocardiography to confirm catheter placement in fluid around the heart (pericardiocentesis), detect anomalous connections within the heart, visualize the right side of the heart and accentuate right sided blood flow for the purpose of quantitation.

Agitated saline contrast echocardiography takes advantage of the increased reflection that results when ultrasound waves meet a liquid/gas interface. This allows for visualization of otherwise poorly reflective areas such as fluid filled cavities by the ultrasound machine. Applications in which this has been clinically useful include echocardiography where agitated saline can be used to define the structural integrity of the interatrial septum or infer the presence of a transpulmonary shunt. Agitated saline can also be combined with Doppler echocardiography to assess blood flow through the tricuspid valve. An alternative method to detect atrial defects uses ultrasound of the brain vessels (transcranial Doppler) to detect bubbles that have crossed from the right heart to the left heart and entered the cerebral circulation.

At present, it may be difficult to generate agitated saline for these studies, and this can result in varying levels of quality and safety. Current bubble studies may have considerable variability in the amount, size, and quantity of bubbles generated. Such imprecise mixtures of saline and air can result in risk to patients and production of false negative studies. In addition, few individuals may be properly trained to safely perform bubble studies. The productivity of an echocardiography lab may be substantially slowed by this lack of trained personnel; and even trained personnel who do not routinely perform agitated saline studies may be reluctant to do so citing concerns about comfort with the procedure.

Described herein is a device and method of producing bubbles (e.g., for an ultrasound-based bubble study). Advantages of the devices and methods described herein may include the production of more uniform and consistently dimensioned bubbles with minimal training. This may result in greater patient safety and comfort as well as studies with improved diagnostic benefit.

Figure 1:
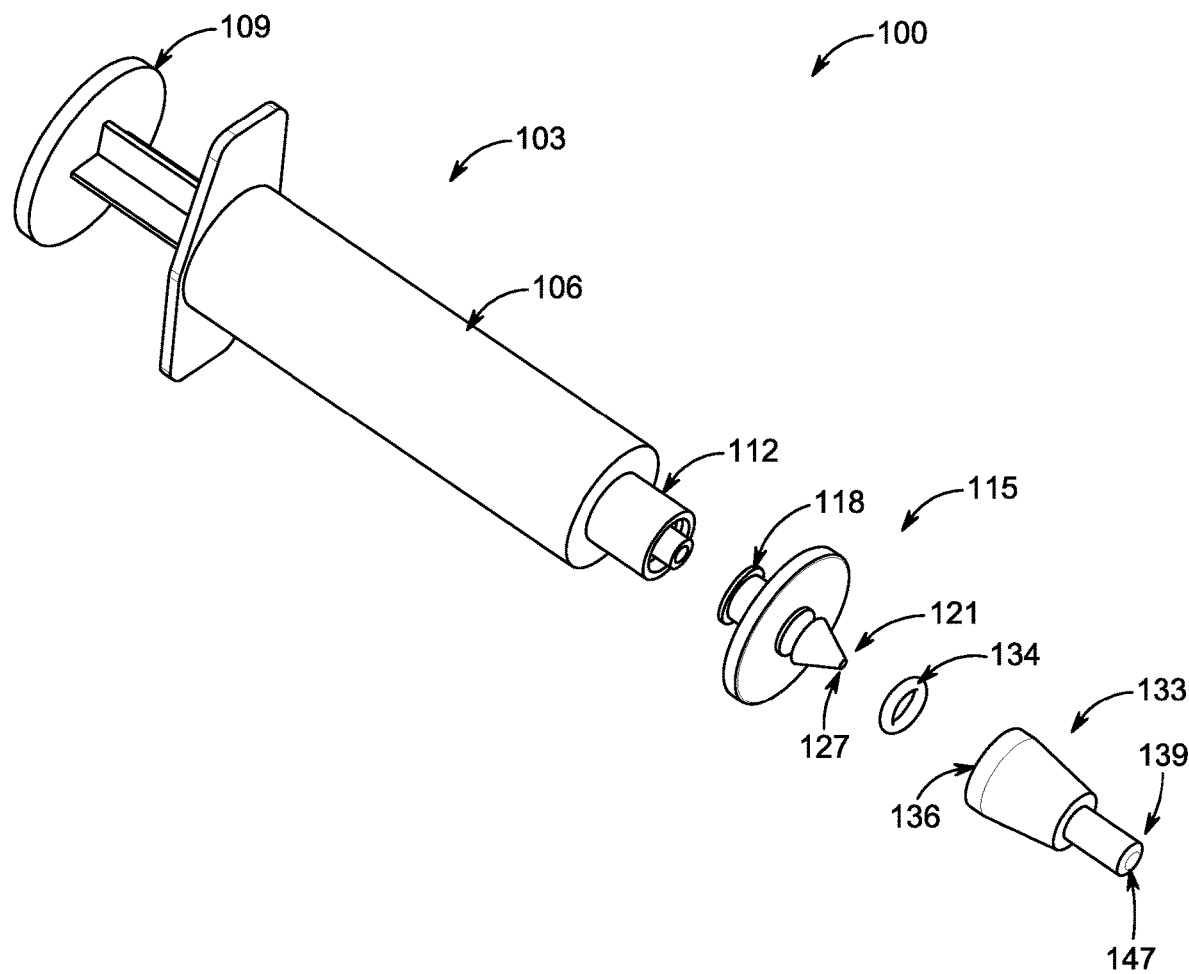
FIG. 1 is an exploded perspective view of an exemplary microbubble generator.

FIG. 1 is an exploded perspective view of an exemplary microbubble generator 100, according to one implementation. As shown, the microbubble generator 100 includes a syringe 103, a converging nozzle 115, and an aerator 133. In operation, the microbubble generator 100 can be coupled to an intravenous (IV) line disposed in a patient undergoing a procedure (e.g., a diagnostic bubble study), and the microbubble generator 100 can be employed to generate microbubbles as a contrast agent.

In some implementations, the syringe 103 portion of the microbubble generator 100 is a standard medical-grade syringe (e.g., 1 mL, 2 mL, 3 mL, 5 mL, 10 mL, 20 mL) having a barrel 106, plunger 109 and tip 112. The syringe 103 may be pre-filled with saline or another fluid that is suitable for intravenous injection, which can provide a vehicle for microbubbles generated by the microbubble generator 100 to be delivered to a target region of a patient's body. The tip 112 can include a Luer lock connector suitable for coupling to needles, catheters, IV lines, etc.

Saline is referenced with respect to various implementations. In some implementations, this could be "NSS," or 0.9% normal saline solution; in other implementations, "45NS," or 0.45% normal saline may be used. In still other implementations, liquids other than saline may be used, such as dextrose in water solution (e.g., "D5W," or 5% dextrose in water; "D10W," or 5% dextrose in water) or other solutions commonly used in intravenous applications at sites that are suitable for diagnostic studies or therapeutic procedures.

The converging nozzle 115, in the implementation shown, has a coupling end 118 that is configured to engage the tip 112 of the syringe 103. In some implementations, the coupling end 118 includes mating Luer lock threads to facilitate a twist-on engagement with the syringe 103. Opposite the coupling end 118 is a converging tip 121. An interior channel 127, which will be described in greater detail with reference to the following figures, is configured to fluidly couple an interior of the syringe 103 to the aerator 133.

The aerator 133, as shown, includes a retention end 136 that is configured to mechanically mate with the converging nozzle 115; and a discharge end 139. In some implementations, the aerator 133 can be coupled to the converging nozzle 115 via a compression-fit coupling facilitated by an O-ring 134 and grooves in the converging nozzle 115 and aerator 133. A discharge channel 147 fluidly couples the interior channel 127 of the converging nozzle 115 to a discharge end 139, which can be configured to engage a catheter or IV port or line used in a bubble study.

In FIG. 1, the syringe 103, converging nozzle 115 and aerator 133 are shown as separate components. In other implementations, however, one or more components may have other arrangements. For example, the converging nozzle 115 and aerator 133 may be ultrasonically welded together, joined with adhesive, snap-fit, etc.; and the converging nozzle 115 or a singular converging nozzle/aerator structure could be coupled to the syringe 103 in one of the foregoing ways or co-molded with and as part of the syringe 103. Additional detail of the exemplary syringe 103, converging nozzle 115 and aerator 133 is now provided with reference to FIGS. 2A, 2B and 2C.

Figure 2A:
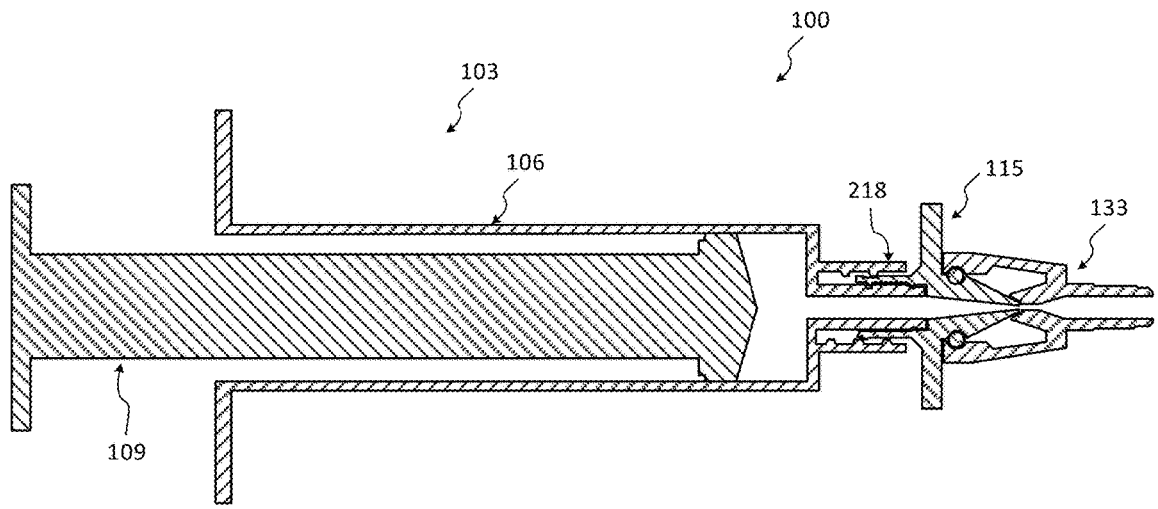
FIG. 2A is a longitudinal cross-section of an exemplary syringe, converging nozzle, and aerator, as they are assembled, in one implementation.

FIG. 2A illustrates a longitudinal cross-section of the syringe 103, converging nozzle 115 and aerator 133, as they could be assembled in some implementations. As shown, the converging nozzle 115 is disposed on the syringe 103 via a Luer lock fitting 218, and the aerator 133 is compression-fit onto the converging nozzle 115 by an O-ring and corresponding grooves in each of the converging nozzle 115 and aerator 133 (see FIG. 2B for detail). In other implementations, connections maybe made differently. For example, other threaded or press-fit connections may replace Luer lock fittings. Similarly, the O-ring and grooves could be replaced by a threaded, adhesive-based or welded connection.

Figure 2B:
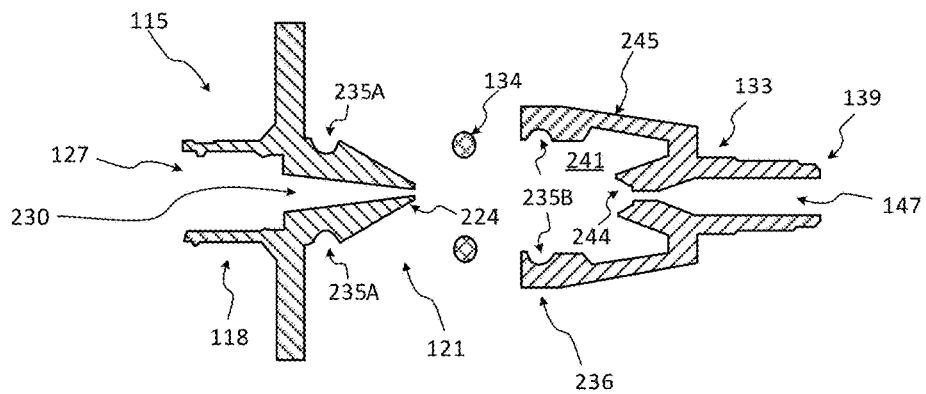
FIG. 2B is a longitudinal cross section of the converging nozzle, O-ring, and aerator shown in FIG. 2A.

FIG. 2B illustrates an exemplary longitudinal cross section of the converging nozzle 115, O-ring 134, and aerator 133. The interior channel 127 fluidly couples to an interior of the mating syringe 103 (see FIGS. 1, 2A) and a throat 230—a portion of the interior channel 127 whose diameter progressively decreases. In operation, the progressively decreasing diameter of the throat 230 changes dynamics of fluid flowing from the syringe 103 and through the converging nozzle 115, as will be described with reference to FIG. 2C.

As shown, the converging nozzle 115 includes grooves 235A for receiving the O-ring 134 and facilitating a compression-fit coupling; and the aerator 133 includes corresponding grooves 235B for the same purpose. This structure allows the O-ring 134 to be slipped into the grooves 235A, and for the retention end 236 of the aerator 133 to be slid over the converging tip 121 and for the grooves 235B to engage and be retained by the O-ring 134. In such an implementation, the O-ring 134 may be made of an elastic material that has sufficient elasticity and compressibility to facilitate engagement of the converging nozzle 115 and aerator 133, and sufficient resilience to securely couple the converging nozzle 115 and aerator 133 once the grooves 235A and 235B of these components 115 and 133 are aligned as described. In some implementations, the O-ring 134 and grooves 235A and 235B may provide an air-tight, sterile seal.

The converging nozzle 115 further includes an external mating surface 224 at the converging tip 121, which is configured to mechanically fit adjacent to a corresponding circumferential lip 244 on the aerator 133. In some implementations, the circumferential lip 244 circumferentially envelopes the external mating surface 224 and abuts the external mating surface 224 at least at one point; in other implementations, the circumferential lip 244 and external mating surface 224 are disposed adjacent and in close proximity to each other. When the converging nozzle 115 and aerator 133 are coupled (e.g., by the grooves 235A and 235B and O-ring 134), the external mating surface 224 and circumferential lip 244 align and facilitate fluid coupling between the interior fluid channel 127 and throat 230, and the discharge channel 147. In some implementations, specific dimensions and geometries of the external mating surface 224 and circumferential lip 244 further facilitate passage of air into the discharge channel 147, from an interior air chamber 241, which is formed by the outer wall 245 of the aerator 133—as will be further described with reference to FIG. 2C.

Figure 2C:
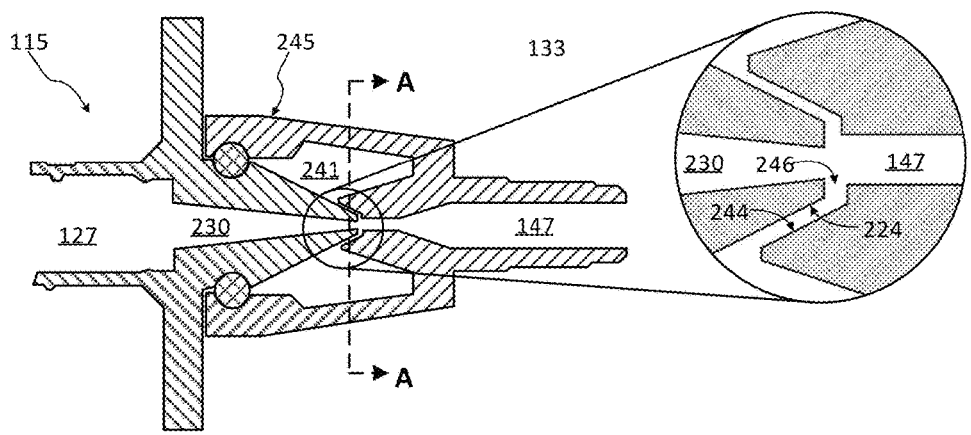
FIG. 2C is another longitudinal cross section of the converging nozzle, O-ring and aerator shown in FIG. 2A.

FIG. 2C is a longitudinal cross section of the converging nozzle 115 and aerator 133, shown in a coupled configuration, and a magnified view of a portion of that cross section. As shown, the interior air chamber 241 is formed by the outer wall 245 of the aerator. A small fluid coupling exists between this interior air chamber 241 and the passageway formed by the interior channel 127, throat 230 and discharge channel 147—specifically by an air channel 246 (see magnified inset) that is configured to exist between the exterior mating surface 224 and the circumferential lip 244. This air channel 246 allows air or other gas in the interior air chamber 241 to be drawn into the aforementioned passageway (throat 230 and discharge channel 147—referred to as the "230/147 passageway"). In addition, this air channel 246 may permit some fluid that is passing through the 230/147 passageway to enter the interior air chamber 241, thereby displacing some of the air there and increasing the pressure in the interior air chamber 241 (e.g., in cases in which there may be a non-negligible back pressure at the discharge channel 147).

Figure 2D:
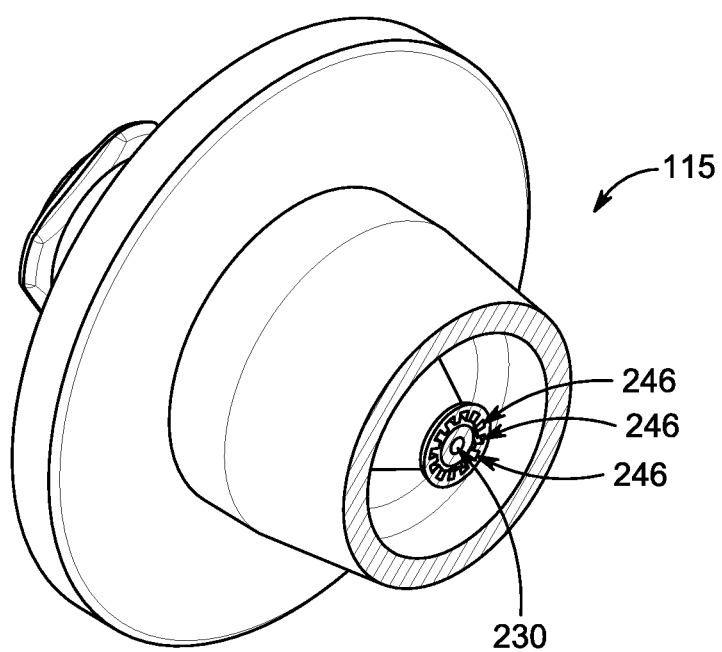
FIG. 2D is a perspective, cross-sectional view of the configuration shown in FIG. 2C.

FIG. 2D is a perspective, cross-sectional view of the converging nozzle 115 shown in FIG. 2C, with the cross section taken along section line A-A. FIG. 2D illustrates the air channel 246 (or series of air channels 246) that fluidly couple the interior air chamber 241 to the throat 230-discharge channel 147 passageway. Visible in FIG. 2D is the throat 230 itself, in the center of the converging nozzle 115, as well as a series of air channels 246 that are disposed radially about throat.

In some implementations, the exterior mating surface 224 and circumferential lip 244 (see FIG. 2C) are in mechanical contact and provide a fluid seal, except at the air channels 246. That is, in such implementations, a fluid coupling between the interior air chamber 241 and the 230/147 passageway only exists at the air channels 246. In some implementations, fewer air channels 246 are provided than shown—for example, some implementations may only include one, two, three or four air channels 246.

Referring back to FIG. 2C, dimensions and geometries of the air channels 246 may be configured to facilitate passage of air from the interior air chamber 241 into the 230/147 passageway only when certain pressure differentials exist therebetween. For example, some implementations may include air channels 246 with very small dimensions and with geometries that promote greater surface tension of any liquid that is disposed in the air channels 246. Specific contours of either or both of the exterior mating surface 224 and the circumferential lip 244 may further promote an increased surface tension of liquid in the air channels 246, to, for example, promote communication of air (and correspondingly, formation of microbubbles) in certain scenarios. Surface treatments to either or both of the exterior mating surface 224 and the circumferential lip 244 (e.g., hydrophobic or hydrophilic coatings) may be employed to further control communication of air or other gas from the interior air chamber 241 to the 230-147 passageway.

In some implementations, a vent (not shown) between the interior air chamber 241 and the exterior of the aerator 133 may be provided to enable more air to be drawn into the fluid than may otherwise be possible. In other implementations, a port or valve (not shown) may be provided to facilitate coupling of an exterior air supply for a similar purpose. In still other implementations, a valve (e.g., a reducing valve—not shown) may be provided to allow fluid to be drained from the air chamber 241 and again be replaced with air—for example, to facilitate an equilibrium relative to back pressure, and to enable the microbubble generator 100 to "recharge" its ability to generate microbubbles.

Figure 2E:
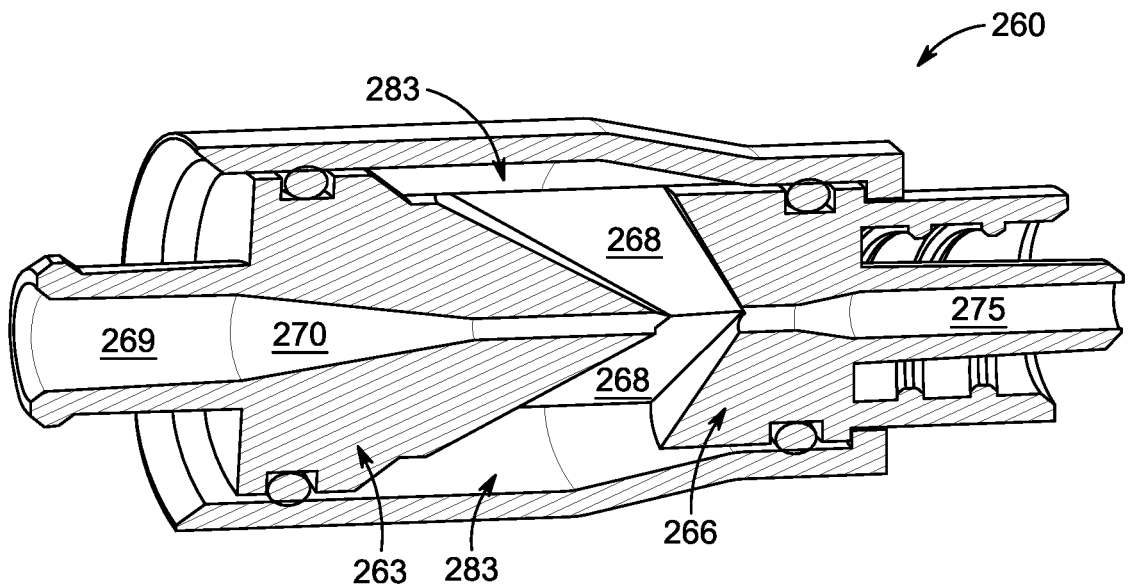
FIG. 2E is a perspective cross-section view of another exemplary converging nozzle and aerator.
Figure 2F:
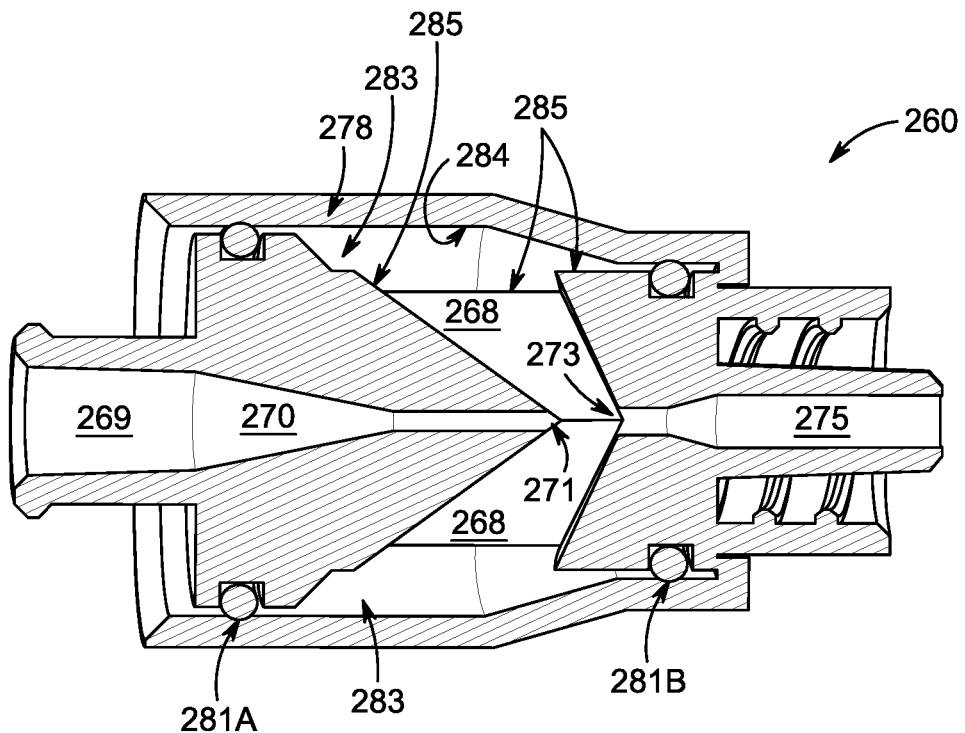
FIG. 2F is a longitudinal cross-section view of the converging nozzle and aerator shown in FIG. 2E.

FIG. 2E illustrates a perspective cross-sectional view of an exemplary implementation 260 of a unitary converging nozzle 263 and aerator 266; and FIG. 2F illustrates a longitudinal cross-section of the same device 260. As shown in this implementation, the converging nozzle 263 and aerator 266 are fabricated as a unitary component (e.g., co-molded), rather than as two separate components. In such a configuration, it may be possible to precisely configure dimensions of one or more air channels 268 and their alignment to a stream of fluid traveling from an interior channel 269, through a section 270 having a progressively decreasing diameter (e.g., a "Venturi section"), out an outlet 271, into an inlet 273 of the aerator 266 and through and out a discharge channel 275.

As shown, the exemplary device 260 includes a housing 278 that surrounds the unitary converging nozzle 263 and aerator 266. In some implementations, as shown, the housing 278 can be sealed to the converging nozzle 263 and aerator 266 by O-rings 281A and 281B. In such implementations, an air chamber 283 is formed (e.g., by an interior surface 284 of the housing 278 and an exterior surface 285 of the unitary component that includes the converging nozzle 263 and aerator 266). When the O-rings 281A and 281B form an airtight and liquid-tight seal (of the air chamber 283, isolating the air chamber 283 from a region exterior to the housing 278 from ingress or egress of gas or liquid via any path other than through the one or more air channels), air (or other gas) in the air chamber 283 can be drawn into a stream of liquid passing through the device 260, in the form of microbubbles.

In some implementations, the exemplary device 260 can operate to produce microbubbles even in the presence of not-insignificant back pressure at the discharge channel 275. Specifically, in the presence of back pressure at the discharge channel 275 (with a robust seal provided by O-rings 281A and 281B), fluid may pass through the interior channel 269, section 270 and into the discharge channel 275. However, no significant volume of fluid may flow out of the discharge channel 275 (e.g., into a downstream intravenous or needle-based system associated with a therapeutic or diagnostic procedure) until pressure is equalized between the device 260 and the back pressure. That is, rather than flowing out of the discharge channel 275, the fluid may initially flow through the air channels 268 and into the interior air chamber 283. Such fluid may displace the air in the air chamber 283, causing an increase in pressure in the air chamber 283.

Once this air pressure increases to the level of the back pressure, fluid may then flow through the device 260, out of the discharge channel 275, and into a connected patient diagnostic or therapeutic system (not shown). In this phase of operation, where the pressure inside the air chamber 283 is nearly equal to the back pressure seen at the discharge channel 275, some air from the air chamber 283 may be drawn into the fluid stream, in the form of microbubbles— via an aspiration effect caused by the pressure drop in the fluid stream itself that is brought about by the increase in speed of flow of that fluid through the Venturi section 270.

Over time, the aspiration of air into the fluid stream may cause the pressure in the air chamber 283 to again drop below a back pressure seen at the discharge channel 275. At this point, some additional fluid may enter the air chamber 283, again displacing air and increasing the pressure inside the air chamber 283. Once equilibrium is reestablished, or nearly reestablished (e.g., within some small percentage, given the dynamic nature of the system, turbulence of the fluid, dynamically varying back pressure, variation in speed of fluid, etc.), air may again be aspirated into the fluid stream in the form of microbubbles.

In some implementations, a one-way reducing valve (not shown) may be provided between the air chamber 283 and an exterior of the housing 278, to enable fluid to be periodically drained from the air chamber 283. Allowing some fluid to be drained from the air chamber 283 may allow, in some implementations, air to be continuously available for aspiration into the fluid stream. In such an implementation, microbubbles may be produced and delivered out of the discharge channel 275 for as long as incoming fluid is supplied through the interior channel 269.

In the implementation shown in FIGS. 2E and 2F, dimensions, geometries and surface treatments (e.g., hydrophobic or hydrophilic coatings) of the air channels 268, the outlet 271 (or interior channel 269 or section 270), the inlet 273 or the discharge channel 275 may be configured to facilitate creation of microbubbles having a specific average size or range of sizes (e.g., an average diameter of less than 2 µm; an average diameter of between about 5 µm and about 10 µm; an average diameter of about 40 µm or less; an average diameter of about 100 µm or less). Such implementations may employ dimensions, geometries or surface treatments to produce regions of turbulent or laminar flow that entrap or aspirate air in a particular manner. In other implementations, specific dimensions, geometries or surface treatments may be employed to create microbubbles with surface tensions or charges that minimize coalescence of microbubbles after they are generated.

Figure 3A:
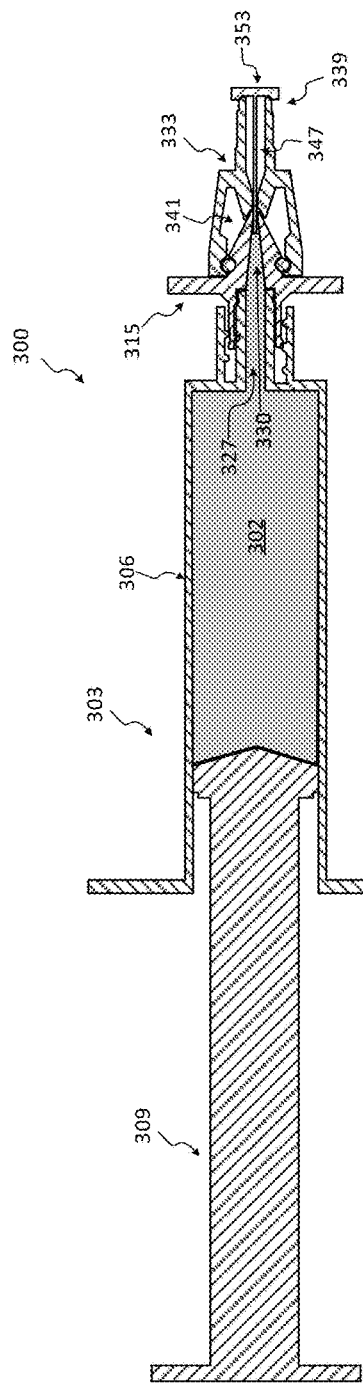
FIGS. 3A, 3B and 3C depict operation of an exemplary microbubble generator.
Figure 3B:
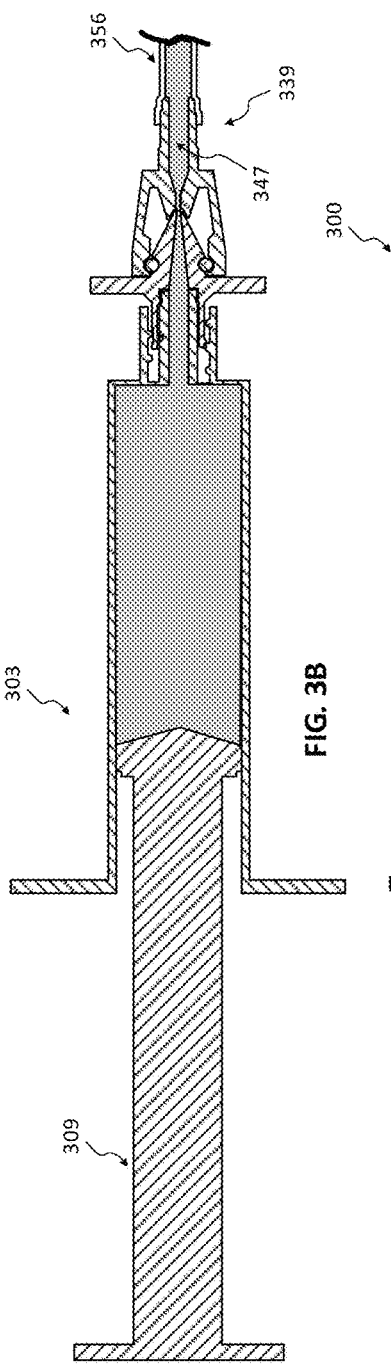
Figure 3C:
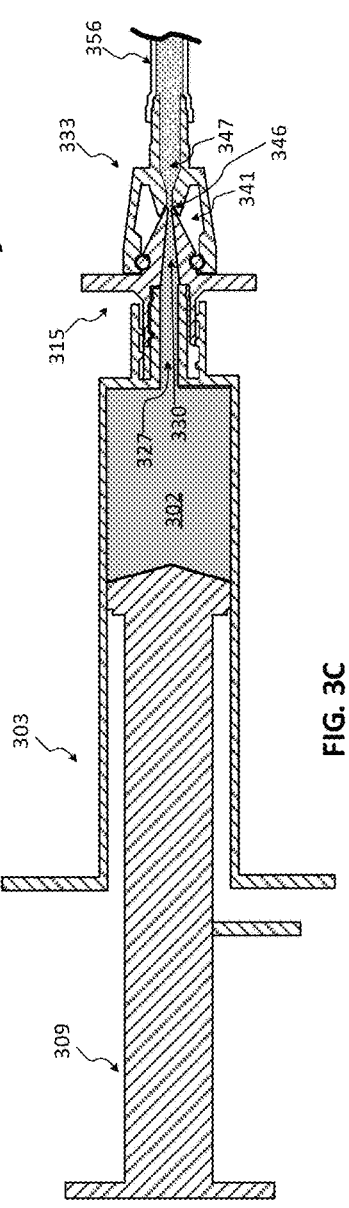

Operation of an overall exemplary microbubble generator 300 are now described with respect to FIGS. 3A, 3B and 3C, in one implementation. As shown in FIG. 3A, a microbubble generator 300 that includes a syringe 303, a converging nozzle 315 and an aerator 333 may be prefilled with a saline solution. That is, saline (or another suitable solution) may be prefilled in an interior 302 of the barrel 306 of the syringe portion 303. To preserve the sterile nature of the saline, and to prevent fluid ingress into an interior chamber 341 of the aerator portion 333, a sealing pin 353 may be provided to seal the saline in the syringe 303, and to seal the interior channel 327 and throat 330 of the converging nozzle 315. In operation, such a pin 353 may be removed immediately prior to use of the microbubble generator 300.

The pin 353 may be made of a corrosion-resistant metal or resilient elastic material that seals off the tip of the throat 330 and a discharge channel 347. The pin 353 may adhesively sealed to the discharge end 339 of the aerator, such that some amount of twisting or pulling force is required by a user to dislodge the pin 353 prior to use of the microbubble generator 300. Such an adhesive seal may further protect the sterile nature of the microbubble generator 300, particularly at the discharge end 339.

In some implementations, the pin 353 may be replaced with an internal membrane (not shown) that retains the saline in the interior 302 of the syringe or in the interior 302 of the syringe and the throat 330 of the converging nozzle 315. In such implementations, a user may be required to depress the plunger 309 in order to generate an internal pressure that is sufficient to overcome the holding force of such a membrane. In some implementations, an internal membrane (not shown) may be configured to be broken when the converging nozzle 315 is affixed to the syringe 303 (e.g., in implementations in which the components are provided separately).

However the contents of the syringe are sealed prior to use, the appropriate seal can be released and the plunger 309 can be depressed slightly to flush microbubble generator 300—as depicted in FIG. 2B. In some instances, this can be done prior to the discharge end 339 being coupled to IV tubing 356 or another connection that may be made to a system used to diagnose or treat a patient (e.g., a needle, catheter, or other apparatus disposed in the patient (not shown)). In other instances, the discharge end 339 may be coupled to IV tubing 356 first, such that the tubing can also be flushed during this initial process.

FIG. 3C depicts the process by which the microbubble generator 300 can generate microbubbles, in one implementation. In particular, after necessary seals are removed, and the microbubble generator 300 is flushed and coupled to a downstream IV system 356 associated with a patient undergoing a diagnostic or therapeutic procedure, the plunger 309 can be further depressed to force fluid from the interior 302 of the syringe 303, into the interior channel 327. In the interior channel 327, the pressure of the fluid is relatively high, and its speed is relatively low (proportional to a speed at which the plunger is depressed). The progressively decreasing diameter of the throat 230 causes the speed of the fluid to increase there, thereby lowering its fluid pressure (through the Venturi effect). This lower pressure of the fluid at the throat 330 draws air into the fluid path traveling from the throat 330 to the discharge channel 347, specifically from the interior chamber 341, via one or more air channels 346—thereby forming microbubbles.

In some implementations, the geometry, dimensions and/or surface treatment of the material forming the air channels 346 is correlated to microbubble size. Thus, in such implementations, configuration of converging nozzle 315 and aerator 333 can cause microbubbles to be created having different sizes and characteristics. In some implementations, microbubbles having a diameter of approximately 5 µm may be created; in other implementations, microbubbles having a diameter of approximately 10 µm may be created; in other implementations, microbubbles having a diameter of about 1-2 μm or less may be created; in other implementations, microbubbles having a diameter of about 40 μm may be created; in other implementations, microbubbles having a diameter up to about 100 μm may be created.

Different sized microbubbles may have different purposes in diagnostic or therapeutic procedures. For example, in certain diagnostic heart procedures, it may be advantageous to create microbubbles of approximately 5 μm to approximately 10 μm in average diameter. As used herein, "about" or "approximately" may mean within 1%, or 5%, or 10%, or 20%, or 50% of a nominal value; and "average" may mean that a significant number (e.g., 25%, 50%, 75%, 80%, 85%, 90%, 95%) of microbubbles have this diameter, or in some implementations, have a diameter that is within one or two standard deviations of the specified diameter. As another example, in diagnosing certain pulmonary conditions, it may be advantageous to create smaller-diameter microbubbles (e.g., 1-2 μm or less). In some implementations, microbubble size may be correlated with coalescence properties of the microbubbles. For example, surface tension and charge of microbubbles (in certain solutions, or in the blood) may inhibit their coalescence; and minimizing such coalescence of microbubbles may be advantageous (e.g., to minimize risk of an air embolism).

In some implementations, it may be advantageous to generate microbubbles of varying sizes. For example, in a procedure to diagnose the existence of a defect in the septum of a patient's heart, it may be advantageous to initially look for the presence of a septum defect with smaller microbubbles; then shift to larger microbubbles to determine whether a closure procedure is warranted. To facilitate procedures in which it may be advantageous to employ microbubbles of varying sizes, multiple microbubble generators may be employed; and in some implementations, they may be coupled together in advance.

FIG. 4 illustrates an exemplary microbubble generating system 400 that employs multiple microbubble generators 401A, 401B and 401C. As shown, each microbubble generator 401A, 401B and 401C can be coupled to a manifold 461 by corresponding fluid lines 456A, 456B and 456C. The manifold can include multi-way valves 464A, 464B and 464C that couple or isolate each fluid line to a main line 465 of the manifold 461; and that main line 465 of the manifold 461 can be coupled to an IV line 458 that is associated with a patient undergoing a diagnostic or therapeutic procedure. In this manner, individual microbubble generators 401A, 401B or 401C can be alternately coupled to the IV line 458 to generate diagnostic or therapeutic microbubbles; or, multiple microbubble generators 401A, 401B or 401C can be simultaneously connected to facilitate delivery of a large volume of fluid with minimal manipulation of valves. Some implementations employ three-way stopcocks 464A, 464B and 464C, as shown, to isolate or fluidly couple one, two or three paths. Other implementations may employ different valve arrangements.

In some implementations, each microbubble generator 401A, 401B or 401C, in a microbubble generating system 400 may be similarly configured to generate microbubbles of the same size. Such implementations may be employed to generate a larger volume of microbubbles, over a longer period of time than would be otherwise possible with a single microbubble generator. In other implementations, each microbubble generator 401A, 401B and 401C may be configured to generate microbubbles of different sizes. For example, microbubble generator 401A may be configured to generate microbubbles having an approximate diameter of 5 μm; microbubble generator 401B may be configured to generate microbubbles having an approximate diameter of 1 μm; and microbubble generator 401C may be configured to generate microbubbles having an approximate diameter of 10 μm. In this manner, complex diagnostic procedures requiring microbubbles of various sizes may be performed with minimal change in equipment.

The exemplary manifold 461 may include a port 468 for flushing out the manifold and/or overall system 400. In some implementations, each microbubble generator 401A, 401B and 401C may have an internal membrane to isolate fluid within a corresponding syringe barrel or syringe barrel/converging nozzle; and discharge channels of each microbubble generator and the manifold itself may be flushed and prefilled with fluid prior to a procedure being performed, through the port 468.

In other implementations, the system 400 may be packaged in a manner in which the syringes, tubing and manifold are all pre-filled with fluid, such that a final connection between a main manifold line 465 and patient IV tubing 458 need be made at the time of a procedure. In such implementations, internal membranes may still be employed in individual microbubble generators 401A, 401B and 401C to prevent egress of fluid into interior air chambers of an aerator component (e.g., air chamber 441A in aerator 433A).

The exemplary system 400 is shown with three microbubble generators 401A, 401B and 401C; but other numbers of microbubble generators could be included—such as, for example, two, four, or five. The microbubble generators 401A, 401B and 401C are shown coupled to the manifold 461 with tubing 456A, 456B, and 456C. In some implementations, various components of the system 400 may be provided and coupled together immediately prior to a patient procedure.

Various implementations described herein may be employed to generate microbubbles for various diagnostic and therapeutic studies. Many such studies involve the human circulatory system. Thus, for reference, portions of a human circulatory system are now briefly described.

Figure 5:
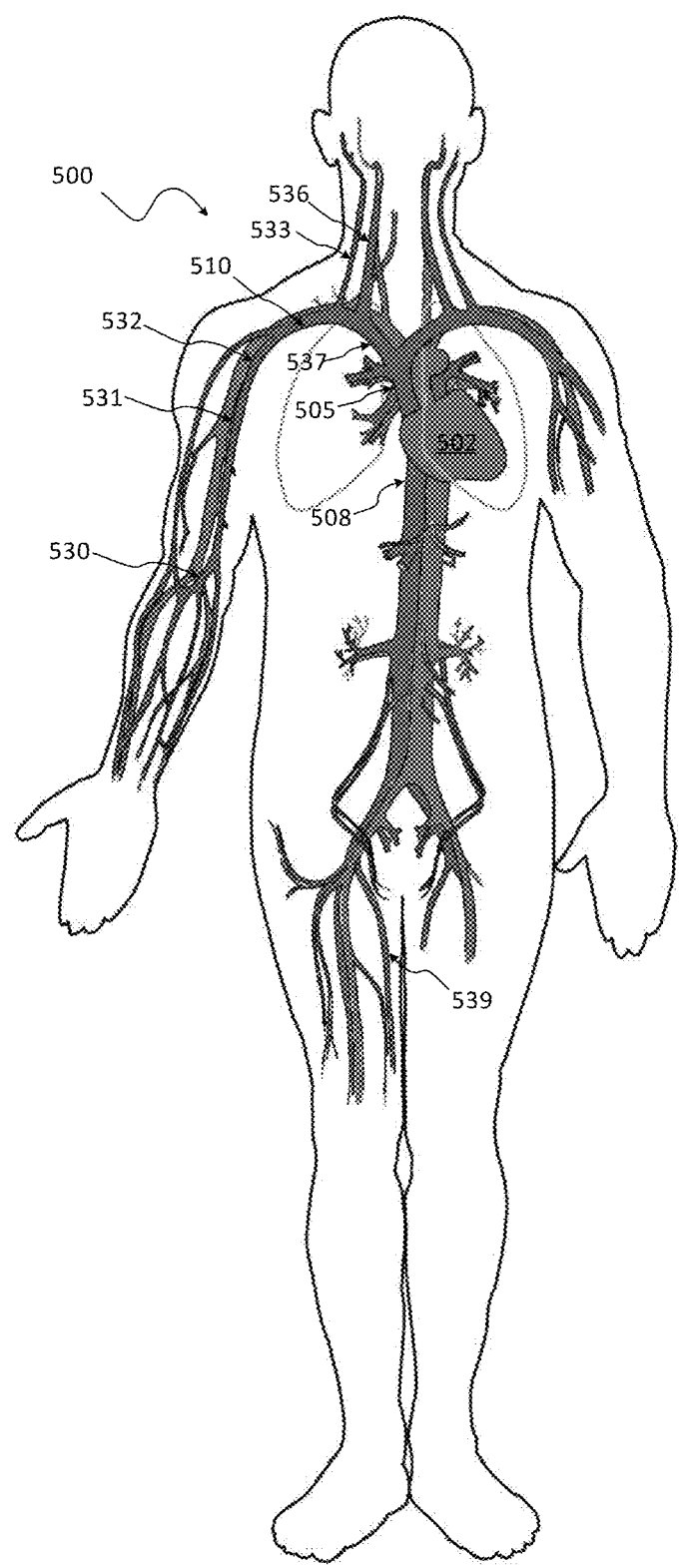
FIG. 5 illustrates a portion of an overall human circulatory system.

FIG. 5 illustrates a portion of an overall human circulatory system 500. At its core, is the heart 502, and a system of arteries that extend from the heart, and veins that return to the heart. Blood is returned to the heart 502 from throughout the body by the vena cava, which is divided into the superior vena cava 505, which collects blood from the upper portion of the body, and the inferior vena cava 508, which collects blood from the lower portion of the body. Blood flows through the superior vena cava 505 and inferior cava 108 on its way to the right atrium.

To facilitate studies whereby microbubbles are to be introduced into the heart and lungs, one must get the bubbles into the venous system and ultimately into the superior vena cava 505 or inferior vena cava 508. With reference to FIG. 5, there are several common access points through which microbubbles can be introduced. Common among them is intravenous introduction of bubbles via the median cubital vein 530 of the right arm. From here, blood flows through the basilic vein 531, axillary vein 532, subclavian vein 510, brachiocephalic vein 537 and into the superior vena cava 505.

Alternative paths to the superior vena cava 513 are the external jugular vein 533 or internal jugular vein 536, both of which drain into a brachiocephalic vein 537 prior to reaching the superior vena cava 505. An alternative route includes the femoral vein 539, which flows into the inferior vena cava 508. Other routes to the superior vena cava 505 and inferior vena cava 508 are possible.

While many implementations are described with reference to heart studies, contrast studies may have other useful applications. For example, microbubbles combined with ultrasound or other imaging technology may be clinically useful in documenting proper catheter placement during pericardiocentesis, or central venous catheter placement in the right atrium and during interventional radiology procedures. In the field of gynecologic ultrasound/infertility, microbubbles may be used to assess patency of the fallopian tubes. Other applications could include imaging of abdominal spaces, portions of the gastrointestinal tract, and joints or other interstitial spaces of a human body. Microbubbles may also be employed in veterinary procedures in a similar manner as described herein.

Several implementations have been described with reference to exemplary aspects, but it will be understood by those skilled in the art that various changes may be made and equivalents may be substituted for elements thereof without departing from the contemplated scope. For example, syringes of various sizes may be employed; a converging nozzle may be integral to the syringe; an aerator may be integral to the converging nozzle; converging nozzles and aerators may be an integral assembly; components may be adhesively joined, ultrasonically welded or molded as unitary parts; some implementations may employ O-rings and compression fittings to join components while other implementations may employ different techniques; different size air channels and geometries may be employed within a converging nozzle; syringes may be prefilled or filled on-site, immediately prior to a procedure; microbubbles may be generated in saline, dextrose, plasma, or other body-compatible fluid; microbubbles may be employed in the context of ultrasound or with other imaging technology; microbubbles may be employed for diagnostic or therapeutic purposes; kits may be provided with any number of microbubble generators, coupled together with a manifold or provided with a manifold for coupling prior to a procedure; different membranes, caps or seals may be employed to contain pre-filled fluid within certain portions of a microbubble generator or microbubble generation system; various numbers of air channels may be employed to facilitate generation of a greater or smaller number of microbubbles per unit of fluid; the air channels may have various dimensions, geometries and/or surface treatment to control size of generated microbubbles; a continuous source of saline or other fluid may replace a syringe; a syringe may be automatically or manually operated.

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A device for generating microbubbles, the device comprising:
    a syringe having a barrel, a plunger and a syringe tip;
    a unitary component having a converging nozzle and aerator;
    a housing component surrounding the unitary component to form an air chamber between an interior surface of the housing component and an exterior surface of the unitary component, the air chamber circumferentially surrounding at least a portion of the unitary component; and
    one or more seals that are disposed between the unitary component and the housing component;
    wherein the converging nozzle has a coupling end, a converging tip opposite the coupling end, and an interior channel that fluidly couples the coupling end and converging tip and has a diameter that progressively decreases from the coupling end to the converging tip, the converging nozzle coupled to the syringe tip at its coupling end;
    wherein the aerator has an inlet that is axially aligned with the interior channel and a discharge channel that is fluidly coupled to the inlet; the unitary component further including one or more air channels that fluidly couple the air chamber and a region adjacent the converging tip and the inlet; and
    wherein the one or more seals isolate the air chamber from a region exterior to the housing component from ingress or egress of gas or liquid via any path other than through the one or more air channels.

2. The device of claim 1, wherein the one or more seals comprise one or more O-rings.

3. The device of claim 1, wherein the syringe is a medical-grade syringe having a capacity of 1 mL, 2 mL, 3 mL, 5 mL, 10 mL or 20 mL.

4. The device of claim 1, wherein at least one of a dimension, a geometry or a surface treatment of the one or more air channels, the converging tip or the inlet is configured to facilitate creation of microbubbles having a surface tension or charge that minimizes coalescence of microbubbles after they are generated.

5. The device of claim 1, wherein at least one of a dimension, a geometry or a surface treatment of the one or more air channels, the converging tip or the inlet is configured to facilitate creation of microbubbles having an average diameter of about 5 μm to about 10 μm.

6. The device of claim 1, wherein at least one of a dimension, a geometry or a surface treatment of the one or more air channels is configured to facilitate creation of microbubbles having an average diameter of about 2 μm or less.

7. The device of claim 1, wherein at least one of a dimension, a geometry or a surface treatment of the one or more air channels, the converging tip or the inlet is configured to facilitate creation of microbubbles having an average diameter of about 40 μm or less or about 100 μm or less.

8. The device of claim 1, wherein the syringe tip and coupling end comprise mating Luer fittings.

9. A device for generating microbubbles, the device comprising:
    a syringe having a barrel, a plunger and a syringe tip;
    a unitary component having a converging nozzle and aerator; and
    a housing component surrounding the unitary component to form an air chamber between an interior surface of the housing component and an exterior surface of the unitary component, the air chamber circumferentially surrounding at least a portion of the unitary component;
    wherein the converging nozzle has a coupling end, a converging tip opposite the coupling end, and an interior channel that fluidly couples the coupling end and converging tip and has a diameter that progressively decreases from the coupling end to the converging tip, the converging nozzle coupled to the syringe tip at its coupling end;
    wherein the aerator has an inlet that is axially aligned with the interior channel and a discharge channel that is fluidly coupled to the inlet; the unitary component further including one or more air channels that fluidly couple the air chamber and a region adjacent the converging tip and the inlet; and a removable sealing pin that, when seated in the discharge channel and interior channel, prevents fluid communication between the air chamber and the discharge channel, the air chamber and interior channel, or the interior channel and discharge channel.

10. The device of claim 9, wherein the removable sealing pin provides a sterile seal that protects the discharge channel.

11. A device for generating microbubbles, the device comprising:
   a medical-grade syringe comprising a barrel, a plunger and a syringe tip;
   a converging nozzle having a coupling end, a converging tip opposite the coupling end, an exterior mating surface adjacent the converging tip, and an interior channel that fluidly couples the syringe tip and converging tip and has a diameter that progressively decreases from the coupling end to the converging tip, the converging nozzle coupled to the syringe tip at its coupling end;
   an aerator comprising a retention end, a discharge end, an interior circumferential lip, a discharge channel at the discharge end, and an interior air chamber that circumferentially surrounds at least one of the converging tip and the interior circumferential lip; wherein the retention end is coupled to the converging nozzle, the interior circumferential lip is disposed adjacent the exterior mating surface, and one or more air channels fluidly couples the discharge channel and the interior air chamber; and
   one or more seals that fixedly isolate the interior air chamber from a region exterior to the aerator from ingress or egress of gas or liquid through any path other than through the one or more air channels.

12. The device of claim 11, wherein at least one of a dimension, a geometry or a surface treatment of the one or more air channels is configured to facilitate creation of microbubbles having a surface tension or charge that minimizes coalescence of microbubbles after they are generated.

13. The device of claim 11, wherein the converging nozzle and aerator each comprise O-ring retention channels, and wherein the aerator and converging nozzle are coupled by an O-ring seated in the O-ring retention channels.

14. The device of claim 11, wherein the converging nozzle and aerator are co-molded together.

15. The device of claim 11, further comprising a removable retention pin that, when seated, prevents fluid communication between the interior air chamber and the discharge channel or interior channel.

16. The device of claim 11, wherein the one or more seals facilitate creation of an equilibrium between a pressure in the air chamber and a back pressure at the discharge channel.

17. A method of generating microbubbles comprising:
   providing a microbubble generator having (a) a syringe having a barrel filled with a body-compatible fluid, a plunger and a syringe tip; (b) a converging nozzle and aerator; (c) a housing surrounding the converging nozzle and aerator to form an air chamber between an interior surface of the housing and exterior surfaces of the converging nozzle and aerator, wherein the air chamber circumferentially surrounds the converging nozzle or aerator; and (d) one or more seals disposed between the housing and the converging nozzle and aerator that isolate the interior air chamber from a region exterior to the housing; wherein the converging nozzle has a coupling end, a converging tip opposite the coupling end, and an interior channel that fluidly couples the coupling end and converging tip and has a diameter that progressively decreases from the coupling end to the converging tip, the converging nozzle coupled to the syringe tip at its coupling end; wherein the aerator has an inlet that is axially aligned with the interior channel and a discharge channel that is fluidly coupled to the inlet; the aerator further including one or more air channels that fluidly couple the air chamber and a region adjacent the converging tip and the inlet;
   coupling the discharge channel to an intravenous line disposed in a patient undergoing a procedure; and
   generating microbubbles by forcing the body-compatible fluid out of the syringe and through the converging nozzle and aerator, into the discharge channel.

18. The method of claim 17, wherein the diameter that progressively decreases causes, via the Venturi effect, air to be extracted from the air chamber, via the one or more air channels, thereby creating microbubbles.

19. The method of claim 17, wherein the body-compatible fluid comprises at least one of saline and dextrose.

20. The method of claim 17 wherein the one or more seals prevent ingress or egress of gas or liquid through any path other than through the one or more air channels to facilitate creation of an equilibrium between a pressure in the air chamber and a back pressure at the discharge channel.

21. A device for generating microbubbles, the device comprising:
   a syringe having a barrel, a plunger and a syringe tip;
   a unitary component having a converging nozzle and aerator;
   a housing surrounding the unitary component to form an air chamber between an interior surface of the housing and an exterior surface of the unitary component, the air chamber circumferentially surrounding a portion of the converging nozzle or the aerator; and
   one or more seals that fixedly isolate the air chamber from a region exterior to the housing;
   wherein the converging nozzle has a coupling end, a converging tip opposite the coupling end, and an interior channel that fluidly couples the coupling end and converging tip and has a diameter that progressively decreases from the coupling end to the converging tip, the converging nozzle coupled to the syringe tip at its coupling end;
   wherein the aerator has an inlet that is axially aligned with the interior channel and a discharge channel that is fluidly coupled to the inlet; the unitary component further including one or more air channels that fluidly couple the air chamber and a region adjacent the converging tip and the inlet; and
   wherein the one or more seals facilitate creation of an equilibrium between a pressure in the air chamber and a back pressure at the discharge channel.

* * * * *